United States Patent [19]

Moran et al.

[11] Patent Number: 4,568,695

[45] Date of Patent: Feb. 4, 1986

[54] 2-AMINO-3-BENZOYL-PHENETHYLAL-COHOLS AND INTERMEDIATES THEREFOR

[75] Inventors: Henry W. Moran; William J. Welstead, Jr., both of Richmond, Va.

[73] Assignee: A. H. Robins Company, Incorporated, Richmond, Va.

[21] Appl. No.: 559,110

[22] Filed: Dec. 7, 1983

[51] Int. Cl.[4] .................. A61K 31/135; C07C 91/40; C07C 97/10
[52] U.S. Cl. .......................... 514/648; 560/9; 560/11; 560/12; 560/47; 560/48; 562/426; 562/436; 562/441; 564/327; 564/328; 564/329
[58] Field of Search .............. 564/327, 328, 329; 424/316, 330; 514/648

[56] References Cited

U.S. PATENT DOCUMENTS 3,192,199 6/1965 McMillan et al. ............... 564/329 X
3,682,892 8/1972 Ning et al. ...................... 564/328 X Primary Examiner—Robert V. Hines

[57] ABSTRACT

Novel 2-amino-3-benzoylphenethylalcohols are provided having the formula:

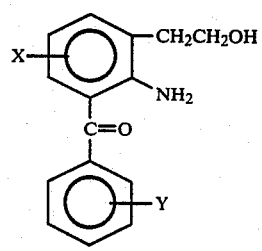

wherein;

X is hydrogen, loweralkyl, loweralkoxy, halogen or trifluoromethyl, and

Y is hydrogen, loweralkyl, loweralkoxy, halogen, trifluoromethyl, —S—loweralkyl,

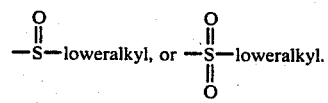

The compounds exhibit anti-inflammatory activity.

20 Claims, No Drawings

2-AMINO-3-BENZOYL-PHENETHYLALCOHOLS AND INTERMEDIATES THEREFOR

BACKGROUND OF THE INVENTION

1. Field of Invention

The present invention relates to certain novel 2-amino-3-benzoyl-phenethylalcohols which have pharmacological activity and pharmaceutical methods and compositions utilizing the same and to certain novel 2-amino-3-[hydroxy(phenyl)methyl]benzeneethanol chemical intermediates used in the preparation thereof.

2. Information Disclosure Statement

2-Amino-3-(5 and 6)benzoylphenylacetic acids, esters, metal salts and hydrates having anti-inflammatory activity are disclosed in U.S. Pat. No. 4,045,576 and U.S. Pat No. 4,126,635. Certain 2-amino-3-(halobenzoyl)methylphenylacetic acids which are also disclosed in copending application U.S. Ser. No. 234,531 filed on Feb. 17, 1981, hereby incorporated by reference, are also starting materials in the preparation of the compounds of this invention. Esters of these and other 2-amino-3-benzoylphenylacetic acids are starting materials in the preparation of compound of the invention.

2-Amino-3-benzoylphenylacetamides having anti-inflammatory activity are disclosed in U.S. Pat. No. 4,313,949.

OBJECTS AND SUMMARY OF THE INVENTION

The novel 2-amino-3-benzoylphenethylalcohols of the present invention are illustrated generally by the following formula:

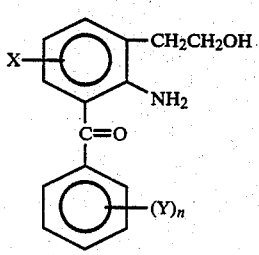

Formula I wherein;
X is selected from the group consisting of hydrogen, loweralkyl, loweralkoxy, halogen or trifluoromethyl,
Y is selected from the group consisting of hydrogen, loweralkyl, loweralkoxy, halogen, trifluoromethyl, S-loweralkyl,

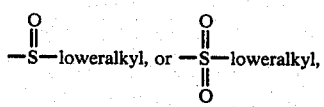

and
n is 1 to 3.

The novel 2-amino-3-[hydroxy(phenyl)methyl]benzeneethanol intermediates are illustrated generally by the formula:

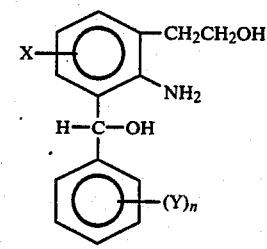

Formula II wherein X is as defined under Formula I and Y is selected from the group consisting of hydrogen, loweralkyl, loweralkoxy, halogen and trifluoromethyl, and n is 1 to 3.

In the further definitions of symbols in the formulas hereof and where they appear elsewhere throughout this specification, the terms have the following significance.

The term "loweralkyl" as used herein includes straight and branched chain radicals of up to eight carbons inclusive and is exemplified by such groups as methyl, ethyl, propyl, isopropyl, butyl, sec. butyl, tertiary butyl, amyl, isoamyl, hexyl, heptyl and octyl radicals and the like. The term "loweralkoxy" has the formula —O-loweralkyl.

The term "halogen" when referred to herein includes fluorine, chlorine, bromine and iodine, preferably fluorine, chlorine and bromine.

The compounds of this invention exhibit excellent anti-inflammatory activity. The compounds also have application as anti-pyretics, analgesics and in inhibiting blood-platelet aggregation.

Anti-inflammatory activity was demonstrated in laboratory animals using a modification of the Evens-Blue Carrageenan Pleural Effusion Assay of Sancilio, L. F., J. Pharmacol. Exp. Ther. 168, 199-204 (1969). See Pharmacology section below.

It is an object of the present invention to provide novel 2-amino-3-benzoyl-phenethylalcohols.

Another object is to provide 2-amino-3-[hydroxy(phenyl)methyl]benzeneethanol chemical intermediates.

A further object is to provide a novel method for the treatment of a living animal body and especially a mammalian body for the purpose of alleviating inflammation utilizing the 2-amino-3-benzoyl-phenethylalcohols and therapeutic compositions therefor.

Additional objects will become apparent to one skilled in the art and still others will become apparent hereinafter.

DETAILED DESCRIPTION OF THE INVENTION AND PREFERRED EMBODIMENTS

The preparation of the compounds of the invention may be accomplished by reaction which involve the following sequence:

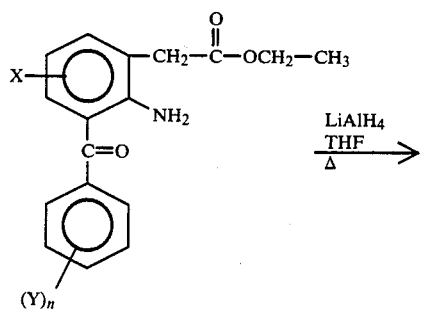

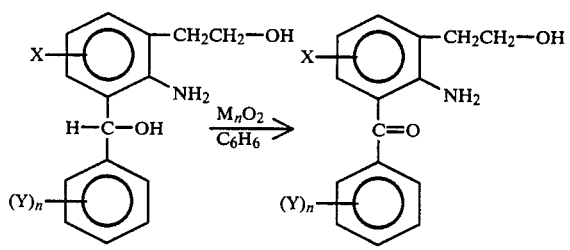

wherein X and Y are as defined hereinabove, except Y cannot be —S-loweralkyl,

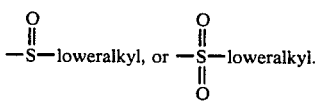

compounds wherein Y is —S-loweralkyl are prepared from compounds of the invention wherein Y is F (fluorine) by the following reaction sequence:

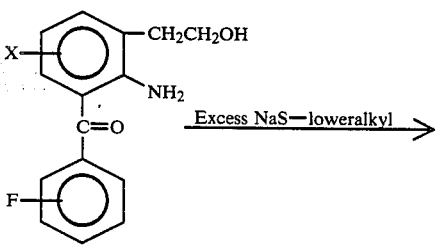

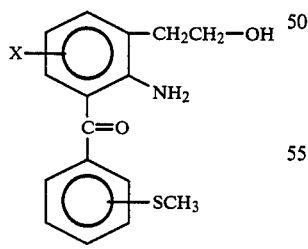

and compounds wherein Y is loweralkyloxythio or loweralkyldioxythio may be prepared by reacting compounds wherein Y is loweralkylthio with 1 or 2 moles of metachloro perbenzoic acid, respectively.

The process for preparing the compounds of the invention is comprised of the following steps:

Step 1—subjecting a (2-amino-3-benzoylphenyl)acetic acid, ethyl ester of the formula:

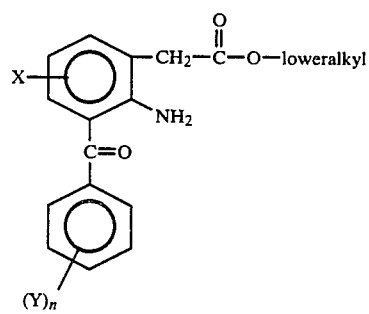

wherein X is as defined above and Y is selected from the group consisting of hydrogen, loweralkyl, loweralkoxy, halogen or trifluoromethyl, and n is 1 to 3 to a hydrogenolysis agent, preferably lithium aluminum hydride in a suitable hot solvent, preferably refluxing tetrahydrofuran to give a compound of the formula:

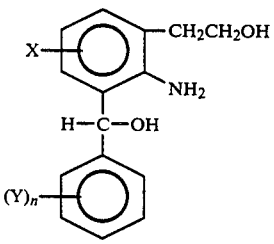

wherein X and Y are the same as the starting values.

Step 2—oxidizing a compound prepared in step 1 with activated manganese dioxide under reflux of a suitable solvent for forming an azeotrope with the liberated water, for example, benzene, to give a compound having the formula:

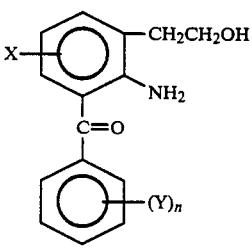

wherein X and Y are the same as the starting values.

Step 3—when required, reacting a compound prepared in step 2 wherein Y is fluoro with an alkali metal salt of a loweralkyl sulfide to give a compound of the formula:

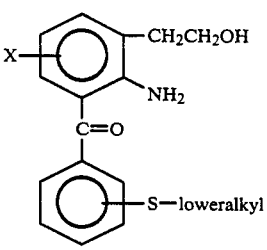

and X is as defined above.

Step 4—when required, reacting a compound prepared in step 3 with an oxidizing agent selected from sodium metaperiodate or metachloroperbenzoic acid to obtain a compound having the formula:

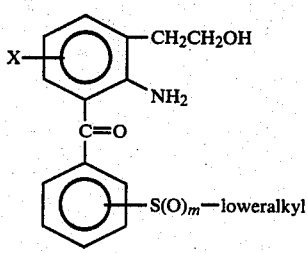

wherein X is as defined above and m is one or two depending on the amount of oxidizing agent used.

The following preparations, intermediates, and examples are presented as a further disclosure and illustration of the compounds of this invention and are not intended as a limitation thereof.

PREPARATION 1

(2-Amino-3-benzoylphenyl)acetic Acid, Ethyl Ester

A solution of 2.5 g (0.009 mole) of (2-amino-3-benzoylphenyl)acetic acid, sodium salt in 25 ml of dry dimethylformamide was treated with 5 g of ethyl iodide (0.035 mole) and stirred with a magnetic stirrer at room temperature for 2 hours. The reaction mixture was then added to water and extracted several times with ethyl ether. The ether extracts, after being washed with water, were dried over sodium sulfate and stripped under vacuum to leave a yellow solid residue. This residue was recrystallized from absolute ethyl alcohol to give 1.7 g (61%) of the titled compound as yellow needles, m.p. 77°–78° C.

Analysis: Calculated for $C_{17}H_{17}NO_3$: C,72.07; H,6.05; N,4.94. Found: C,72.33; H,5.83; N,5.07.

PREPARATION 2

2-Amino-3-benzoyl-5-chlorobenzeneacetic Acid, Ethyl Ester

A solution of 3.12 g (0.1 mole) of 2-amino-3-benzoyl-5-chlorobenzeneacetic acid, sodium salt.½ H$_2$O in 250 ml of dry dimethylformamide was treated with 44 g of ethyl iodide (0.3 mole) under nitrogen and stirred for 2 hours. The resulting solution was then added to one liter of water and extracted several times with ethyl ether. The combined ether layers were washed with water, dried over sodium sulfate, filtered and stripped to yield a solid yellow residue. This residue was recrystallized from ethyl alcohol, yielding 1.5 g of the title compound as yellow needles, m.p. 80°–82° C.

Analysis: Calculated for $C_{17}H_{16}ClNO_3$: C64.26; H,5.08; N,4.41. Found: C,64.17; H,5.01; N,4.39.

PREPARATION 3

2-Amino-3-(4-chlorobenzoyl)benzeneacetic Acid, Ethyl Ester

Fourteen g of 2-amino-3-(4-chlorobenzoyl)benzene acetic acid, sodium salt.H$_2$O was dissolved in 150 ml of dimethylformamide and then treated with 30 g of ethyl iodide. The resulting solution was stirred at room temperature for 2.5 hours. The solution was then added to water and the mixture was extracted several times with benzene. The benzene layer obtained was washed with dilute base and water, dried over sodium sulfate and stripped to leave an oil which crystallized on trituration with pet. ether. Recrystallization from ethyl alcohol gave 11.6 g of the titled compound as yellow flakes, m.p. 101°–102° C.

Analysis: Calculated for $C_{17}H_{16}ClNO_3$: C,64.26; H,5.08; N,4.41. Found: C,65.14; H,5.06; N,4.51.

PREPARATION 4

2-Amino-3-(4-bromobenzoyl)benzeneacetic acid ethyl ester

A slurry of 35.6 g (0.1 mole) of 2-amino-3-(4-bromobenzoyl)benzeneacetic acid, sodium salt in 500 ml of dimethylformamide was treated with 32.0 g (0.2 mole) of ethyl iodide and stirred at ambient temperature for 24 hr. The mixture was filtered and the filtrate was poured into 3.5 liters of water. The solid which precipitated was collected by filtration, washed with water and recrystallized from absolute ethanol to yield 26.8 g (74%) of the titled compound as tiny gold needles, m.p. 107°–109° C.

Analysis: Calculated for $C_{17}H_{16}BrNO_3$: C,56.37; H,4.45; N,3.87. Found: C56.22; H,4.42; N,3.87.

INTERMEDIATE 1

2-Amino-3-[hydroxy(phenyl)methyl]benzeneethanol

A suspension of 5.5 g (0.145 mole) of lithium aluminum hydride in 60 ml of dry tetrahydrofuran was treated with 19.4 g (0.0685 mole) of 2-amino-3-benzoyl benzeneacetic acid, ethyl ester dissolved in 120 ml of dry tetrahydrofuran stirred under nitrogen. After addition was complete, the mixture was continued at reflux for 2 hours. The mixture was then cooled, treated with successive additions of 5.5 ml of water, 5.5 ml of 15% sodium hydroxide and 16.5 ml of water. The mixture was then filtered, the filtrate stripped and the residue recrystallized from toluene. The titled compound (10.2 g) was obtained as pinkish needles, m.p. 101° C.

Analysis: Calculated for $C_{15}H_{17}NO_2$: C,74.05; H,7.04; N,5.76. Found: C,74.13; H,7.00; N,5.66.

INTERMEDIATE 2

2-Amino-5chloro-3-[hydroxy(phenyl)methyl]benzeneethanol

A solution of 15.85 g (0.05 mole) of 2-amino-3-benzoyl-5-chlorobenzeneacetic acid, ethyl ester dissolved in 100 ml of dry tetrahydrofuran was added dropwise to a suspension of 4.0 g (0.105 mole) of lithium aluminum hydride in 50 ml of dry tetrahydrofuran. Gentle reflux was maintained during the addition. Reflux was continued for 2 hours after completion of the addition. The mixture was cooled and carefully treated with 4 ml of water, 4 ml of 15% sodium hydroxide and 12 ml of water. The resulting mixture was filtered, the filtrate stripped and the resulting residue recrystallized from toluene. The titled compound, 10.5 g (70%) having a m.p. of 130°–132° C. was obtained.

Analysis: Calculated for $C_{15}H_{16}ClNO_2$: C,64.87; H,5.81; N,5.04. Found: C,64.60; H,5.74; N,5.03.

INTERMEDIATE 3

2-Amino-3-[(4-chlorophenyl)hydroxymethyl]benzeneethanol

To a slurry of 5.5 g (0.145 mole) of lithium aluminum hydride in 50 ml of dry tetrahydrofuran was added dropwise a solution of 21.9 g (0.069 mole) of 2-amino-3-(4-chlorobenzoyl)benzeneacetic acid, ethyl ester in 120 ml of dry tetrahydrofuran. After the addition was complete, the mixture was heated at reflux under a nitrogen atmosphere for 2.5 hours. The mixture was cooled and treated successively with 5.5 ml of water, 5.5 ml of 5% sodium hydroxide and 16.5 ml of water. The mixture was filtered through celite and the filter cake was washed several times with tetrahydrofuran. The combined filtrates were concentrated to give a solid residue. This residue was recrystallized from ethyl acetate to yield 8.6 g (45%) of the titled compound as fluffy white needles, m.p. 132°–134° C.

Analysis: Calculated for $C_{15}H_{16}ClNO_2$: C,64.87; H,5.81; N,5.04. Found: C,65.17; H,5.84; N,5.18.

INTERMEDIATE 4

2-Amino-3-[(4-bromophenyl)hydroxymethyl]benzeneethanol

To a stirred slurry of 3.3 g (0.087 mole) of lithium aluminum hydride in 75 ml of dry tetrahydrofuran a solution of 15.8 g (0.043 mole) of 2-amino-3-(4-bromobenzoyl) benzeneacetic acid, ethyl ester in 175 ml of tetrahydrofuran was added dropwise over a 20 min period. The mixture was then heated at reflux for 1.5 hr under nitrogen atomsphere. The mixture was cooled and treated successively with 3.3 ml of water, 3.3 ml of a 5% sodium hydroxide solution and 10 ml of water. The mixture was filtered through celite and the filter cake was washed thoroughly with tetrahydrofuran. The combined filtrate and tetrahydrofuran wash was concentrated under reduced pressure to give a solid residue. The solid was recrystallized from ethyl acetate to yield 7.6 g (54%) of the titled compound as gray solid, m.p. 128°–129° C.

Analysis: Calculated for $C_{15}H_{16}BrNO_2$: C,55.92; H,5.01; N,4.35. Found: C,56.28; H,5.08; N,4.44.

INTERMEDIATE 5

Utilizing the procedure of Intermediate 4 and substituting the following esters for 2-amino-3-(4-bromobenzoyl)benzeneacetic acid, ethyl ester:

2-amino-3-benzoyl-5-methoxybenzeneacetic acid, ethyl ester,
2-amino-3-(3,4-dimethoxybenzyl)-benzeneacetic acid, ethyl ester,
2-amino-3-(4-fluorobenzoyl)-benzeneacetic acid, ethyl ester,
2-amino-3-(4-methoxybenzoyl)-benzeneacetic acid, ethyl ester,
2-amino-3-(4-iodobenzoyl)-5-chlorobenzeneacetic acid, ethyl ester,
2-amino-3-(4-bromobenzoyl)-5-bromobenzeneacetic acid, ethyl ester,
2-amino-3-(4-bromobenzoyl)-5-chlorobenzeneacetic acid, ethyl ester,
2-amino-3-(4-bromobenzoyl)-5-fluorobenzeneacetic acid, ethyl ester,
2-amino-3-(4-fluorobenzoyl)-5-methylbenzeneacetic acid, ethyl ester,
2-amino-3-(2,4-dichlorobenzoyl)-5-methylbenzeneacetic acid, ethyl ester,
2-amino-3-(4-bromobenzoyl)-5-methylbenzeneacetic acid, ethyl ester,
2-amino-3-(2-chloro-4-bromobenzoyl)-benzeneacetic acid, ethyl ester,
2-amino-3-(2-chloro-4-bromobenzoyl)-5-chlorobenzeneacetic acid, ethyl ester,
2-amino-3-(3,4,5-trimethoxybenzoyl)-5-chlorobenzeneacetic acid, ethyl ester,
2-amino-3-(4-methylbenzoyl)-5-chlorobenzeneacetic acid, ethyl ester,
2-amino-3-[4-(trifluoromethyl)-benzoyl]-5-chlorobenzeneacetic acid, ethyl ester, and
2-amino-3-benzoyl-5-trifluoromethylbenzeneacetic acid, ethyl ester, there are obtained:
2-amino-3-[hydroxy(phenyl)methyl]-5-methoxybenzeneethanol,
2-amino-3-[hydroxy(3,4-dimethoxyphenyl)methyl]benzeneethanol,
2-amino-3-[hydroxy(4-fluorophenyl)methyl]benzeneethanol,
2-amino-3-[hydroxy(4-methoxyphenyl)methyl]benzeneethanol,
2-amino-5-chloro-3-[hydroxy(4-iodophenyl)methyl]benzeneethanol,
2-amino-5-bromo-3-[hydroxy(4-bromophenyl)methyl]benzeneethanol,
2-amino-5-chloro-3-[hydroxy(4-bromophenyl)methyl]benzeneethanol,
2-amino-5-fluoro-3-[hydroxy(4-bromophenyl)methyl]benzeneethanol,
2-amino-3-[hydroxy(4-fluorophenyl)methyl]-5-methylbenzeneethanol,
2-amino-3-[hydroxy(2,4-dichlorophenyl)methyl]-5-methylbenzeneethanol,
2-amino-3-[hydroxy(4-bromophenyl)methyl]-5-methylbenzeneethanol,
2-amino-3-[hydroxy(4-bromo-2-chlorophenyl)methyl]benzeneethanol,
2-amino-5-chloro-3-[hydroxy(4-bromo-2-chlorophenyl)methyl]benzeneethanol,
2-amino-5-chloro-3-[hydroxy(3,4,5-trimethoxyphenyl)methyl]benzeneethanol,
2-amino-5-chloro-3-[hydroxy(4-methylphenyl)methyl]benzeneethanol,
2-amino-5-chloro-3-[hydroxy[4-(trifluoromethyl)-phenyl]methyl]benzeneethanol, and
2-amino-3-[hydroxy(phenyl)methyl]-5-(trifluoromethyl)benzeneethanol.

EXAMPLE 1

[2-Amino-3-(2-hydroxyethyl)phenyl]phenylmethanone

A suspension of 7.7 g of 2-amino-3-[hydroxy(phenyl)methyl]benzene ethanol in 250 ml of benzene was treated with 14 g of activated Manganese dioxide and refluxed for 5 hours using a Dean-Stark trap. The hot mixture obtained was then filtered through Celite and the filtrate stripped to yield a dark oil. The oily material was placed on a florisil column and eluted with a benzene-acetone mixture. The isolated product was recrystallized from ethanol-pet. ether (30:60) to give the titled compound as yellow needles, m.p. 107°–108° C.

Analysis: Calculated for $C_{15}H_{15}NO_2$: C,74.67; H,6.27; N,5.81. Found: C,74.62; H,6.29; N,5.78.

EXAMPLE 2

[2-Amino-5-chloro-3-(2-hydroxyethyl)phenyl]phenylmethanone

A suspension of 14 g (0.05 mole) of 2-amino-5-chloro-3-[hydroxy(phenyl)methyl]benzene ethanol in 500 ml of benzene was treated with 23 g (0.25 mole) of activated manganese dioxide and brought to reflux in a vessel fitted with a Dean-Stark trap. After 5 hours the hot mixture was filtered through Celite and the benzene stripped to yield a yellow material. This material was recrystallized from ethanol:pet. ether (30:60) to give 10.8 g of the titled compound, m.p. 135°–137° C.

Analysis: Calculated for $C_{15}H_{14}ClNO_2$: C,65.34; H,5.12; N,5.08. Found: C,65.22; H,5.19; N,5.07.

EXAMPLE 3

[2-Amino-3-(2-hydroxyethyl)phenyl](4-chlorophenyl)methanone

A mixture of 6.0 g (0.022 mole) of 2-amino-3-[(4-chlorophenyl)hydroxymethyl]benzene ethanol, 8.7 g (0.10 mole) of activated manganese dioxide and 250 ml of benzene was heated at reflux utilizing a Dean-Stark trap for 5 hours. The hot mixture obtained was filtered through Celite and the filtrate was concentrated to give a solid residue. This residue was recrystallized successively from carbon tetrachloride, cyclohexane and benzene, and 2-propanol to yield 2.9 g (48%) of the titled compound as a yellow solid,
m.p. 111°–126° C.

Analysis: Calculated for $C_{15}H_{14}ClNO_2$: C,65.34; H,5.12; N,5.08. Found: C,65.45; H,5.21; N,5.14.

EXAMPLE 4

[2-Amino-3-(2-hydroxyethyl)phenyl](4-bromophenyl)methanone

A mixture of 5.3 g (0.016 mole) of 2-amino-3-[(4-bromophenyl)hydroxymethyl]benzeneethanol, 7.1 g (0.08 mole) of manganese dioxide and 250 ml of benzene was heated at reflux for 20 hr. utilizing a Dean-Stark trap for water removal. The mixture was filtered through celite and the filtrate was concentrated under reduced pressure to give 4.8 g of brown gum as residue. The residue was purified by column chromatography on 100 g of silica gel and the product was eluted with 15% ethyl acetate in benzene. The fractions containing the title compound were combined and concentrated under reduced pressure to give a solid residue. The solid was recrystallized from cyclohexane benzene to give 1.6 g (30%) of the titled compound as orange flakes, m.p. 126°–127° C.

Analysis: Calculated for $C_{15}H_{14}BrNO_2$: C56.27; H,4.41; N,4.38. Found: C,56.52; H,4.42; N,4.34.

EXAMPLE 5

Utilizing the techniques of Examples 1–4 and substituting the following intermediates:
2-amino-3-[hydroxy(phenyl)methyl]-5-methoxybenzeneethanol,
2-amino-3-[hydroxy(3,4-dimethoxyphenyl)methyl]benzeneethanol,
2-amino-3-[hydroxy(4-fluorophenyl)methyl]benzeneethanol,
2-amino-3-[hydroxy(4-methoxyphenyl)methyl]benzeneethanol,
2-amino-5-chloro-3-[hydroxy(4-iodophenyl)methyl]benzeneethanol,
2-amino-5-bromo-3-[hydroxy(4-bromophenyl)methyl]benzeneethanol,
2-amino-5-chloro-3-[hydroxy(4-bromophenyl)methyl]benzeneethanol,
2-amino-5-fluoro-3-[hydroxy(4-bromophenyl)methyl]benzeneethanol,
2-amino-3-[hydroxy(4-fluorophenyl)methyl]-5-methylbenzeneethanol,
2-amino-3-[hydroxy(2,4-dichlorophenyl)methyl]-5-methylbenzeneethanol,
2-amino-3-[hydroxy(4-bromophenyl)methyl]-5-methylbenzeneethanol,
2-amino-3-[hydroxy(4-bromo-2-chlorophenyl)methyl]benzeneethanol,
2-amino-5-chloro-3-[hydroxy(4-bromo-2-chlorophenyl)methyl]benzeneethanol,
2-amino-5-chloro-3-[hydroxy(3,4,5-trimethoxyphenyl)methyl]benzeneethanol,
2-amino-5-chloro-3-[hydroxy(4-methylphenyl)methyl]benzeneethanol,
2-amino-5-chloro-3-[hydroxy[4-(trifluoromethyl)phenyl]methyl]benzeneethanol, and
2-amino-5-trifluoromethyl-3-[hydroxy(phenyl)methyl]-4-chlorobenzeneethanol.
there are obtained:
[2-amino-5-methoxy-3-(2-hydroxyethyl)phenyl]phenylmethanone,
[2-amino-3-(2-hydroxyethyl)phenyl]-(3,4-dimethoxyphenyl)methanone,
[2-amino-3-(2-hydroxyethyl)phenyl]-(4-fluorophenyl)methanone,
[2-amino-3-(2-hydroxyethyl)phenyl]-(4-methoxyphenyl)methanone,
[2-amino-5-chloro-3-(2-hydroxyethyl)phenyl]-(4-iodophenyl)methanone,
[2-amino-5-bromo-3-(2-hydroxyethyl)phenyl]-(4-bromophenyl)methanone,
[2-amino-5-chloro-3-(2-hydroxyethyl)phenyl]-(4-bromophenyl)methanone,
[2-amino-5-fluoro-3-(2-hydroxyethyl)phenyl]-(4-bromophenyl)methanone,
[2-amino-5-methyl-3-(2-hydroxyethyl)phenyl]-(4-fluorophenyl)methanone,
[2-amino-5-methyl-3-(2-hydroxyethyl)phenyl]-(2,4-dichlorophenyl)methanone,
[2-amino-5-methyl-3-(2-hydroxyethyl)phenyl]-(4-bromophenyl)methanone,
[2-amino-3-(2-hydroxyethyl)phenyl]-(2-chloro-4-bromophenyl)methanone,
[2-amino-5-chloro-3-(2-hydroxyethyl)phenyl]-(2-chloro-4-bromophenyl)methanone,
[2-amino-5-chloro-3-(2-hydroxyethyl)phenyl]-(3,4,5-trimethoxyphenyl)methanone,
[2-amino-5-chloro-3-(2-hydroxyethyl)phenyl]-(4-methylphenyl)methanone,
[2-(amino-5-chloro-3-(2-hydroxyethyl)phenyl]-[4-(trifluoromethyl)phenyl]methanone, and
[2-amino-5-trifluoromethyl-3-(2-hydroxyethyl)phenyl](4-chlorophenyl)methanone.

EXAMPLE 6

[2-Amino-3-(2-hydroxyethyl)phenyl][(4-methylthio)phenyl]methanone

2-Amino-3-[hydroxy(4-fluorophenyl)methyl]benzeneethanol is reacted with sodium methyl mercaptide in a suitable solvent to give the title compound.

EXAMPLE 7

[2-Amino-3-(2-hydroxyethyl)phenyl][(4-methylsulfinyl)phenyl]methanone

[2-Amino-3-(2-hydroxyethyl)phenyl]-[(4-methylthio)phenyl]methanone is treated cautiously at about 0° C. with an equal molar amount of meta-chloroperbenzoic acid in a suitable solvent and the mixture poured into dilute aqueous sodium hydroxide of equal molar amount to give the title compound.

EXAMPLE 8

[2-Amino-3-(2-hydroxyethyl)phenyl]-[(4-methylsulfonyl)phenyl]methanone

[2-Amino-3-(2-hydroxyethyl)phenyl][(4-methylthio)phenyl]methanone was treated with 2 molar equivalents each of meta chlorobenzoic acid and sodium hydroxide solution in the same manner as in Example 7.

PHARMACOLOGY

The response of the 2-amino-3-benzoylphenethyl alcohols of the present invention in the above-mentioned Carrageenan Pleural Effusion Assay was measured in comparison to indomethacin. Each of the compounds were tested against indomethacin as they were synthesized which resulted in more than one comparative test at different times as follows:

| Test Compound | Dose mg/kg. | Reduction In Pleural Effusion, Vol. % |
|---|---|---|
| Example 1 | 100 | −40 |
| " | 4 | −21 |
| Indomethacin | 4 | −19 |
| Example 3 | 100 | −43 |
| " | 4 | −25 |
| Indomethacin | 4 | −42 |
| Example 4 | 4 | −26 |
| Indomethacin | 4 | −23 |

In addition, in another test, the compound of Example 4 and indomethacin were administered at several different dosages in the above Carrageenan Plural Effusion Assay and dose response curves were prepared for each and compared by regression analysis over the length of the curves. This comparison showed that the compound of Example 4 was 1.26 times as potent as indomethacin.

FORMULATION AND ADMINISTRATION

The present invention also contemplates novel compositions containing the compounds of the invention as active ingredients. Effective quantities of any of the foregoing pharmacologically active compounds may be administered to a living animal body in any one of various ways, for example, orally as in capsules or tablets, parenterally in the form of sterile solutions or suspensions, and in some cases intravenously in the form of sterile solutions. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmacologically active compounds may be advantageously employed in a unit dosage of from 0.1 to 250 milligrams or more depending on the size of the animal. For example, a large animal such as a horse may require tablets of 500–1000 mg active ingredient. The unit dosage may be given a suitable number of times daily so that the daily dosage may vary from 0.3 to 450 milligrams. Five to 25 milligrams appears optimum per unit dose.

It is only necessary that the active ingredient constitute an effective amount, i.e., such that a suitable effective dosage will be obtained consistent with the dosage form employed. The exact individual dosages as well as daily dosages will, of course, be determined according to standard medical principles under the direction of a physician or veterinarian.

The active agents of the invention may be combined with other pharmacologically active agents, or with buffers, antacids or the like, for administration and the proportion of the active agent in the compositions may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | Per capsule, mg. |
|---|---|
| Active ingredient | 5.0 |
| Lactose | 296.7 |
| Starch | 129.0 |
| Magnesium stearate | 4.3 |
| Total | 435.0 mg. |

Additional capsule formulations preferably contain a higher dosage of active ingredient and are as follows.

| Ingredients | Per capsule, mg. |
|---|---|
| Active ingredient | 25.0 |
| Lactose | 306.5 |
| Starch | 99.2 |
| Magnesium stearate | 4.3 |
| Total | 435.0 mg. |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

|  | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
|  | 170.1 mg. |

Uniformly blend 1, 2, 4, and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

3. Injectable-2% sterile solutions.

|  | Per cc. |
| --- | --- |
| Active ingredient | 20 mg. |
| Preservative, e.g., cholorobutanol | 0.5% weight/volume |
| Water for injection | q.s. |

Prepare solutions, clarify by filtration, fill into vials, seal and autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. A compound selected from the group having the formula:

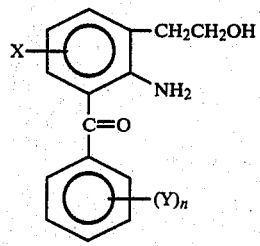

wherein;
X is hydrogen, loweralkyl, loweralkoxy, halogen or trifluoromethyl,
Y is hydrogen, loweralkyl, loweralkoxy, halogen, trifluoromethyl, —S-loweralkyl,

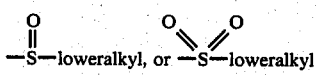

and n is 1–3.

2. The compound of claim 1 which is [2-amino-3-(2-hydroxyethyl)phenyl]phenylmethanone.
3. The compound of claim 1 which is [2-amino-5-chloro-3-(2-hydroxyethyl)phenyl]phenylmethanone.
4. The compound of claim 1 which is [2-amino-3-(2-hydroxyethyl)phenyl](4-chlorophenyl)methanone.
5. The compound of claim 1 which is [2amino-3-(2-hydroxyethyl)phenyl](4-bromophenyl)methanone.
6. A method of alleviating inflammation in a living animal body comprising internally administering to said animal an effective amount of a compound selected from the group having the formula:

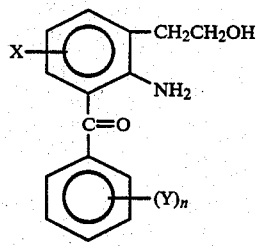

wherein;
X is hydrogen, loweralkyl, loweralkoxy, halogen or trifluoromethyl, and
Y is hydrogen, loweralkyl, loweralkoxy, halogen, trifluoromethyl, —S-loweralkyl,

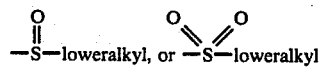

and n is 1–3.

7. The method of claim 6 wherein the compound is [2-amino-3-(2-hydroxyethyl)phenyl]phenylmethanone.
8. The method of claim 6 wherein the compound is [2-amino-5-chloro-3-(2-hydroxyethyl)phenyl]phenylmethanone.
9. The method of claim 6 wherein the compound is [2-amino-3-(2hydroxyethyl)phenyl](4-chlorophenyl)methanone.
10. The method of claim 6 wherein the compound is [2-amino-3-(2-hydroxyethyl)phenyl](4-bromophenyl)methanone.
11. A therapeutical composition suitable for alleviating inflammation in a living animal body comprising
(a) an effective amount of a compound selected from the group having the formula:

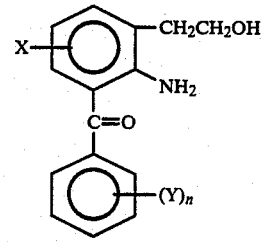

wherein;
X is hydrogen, loweralkyl, loweralkoxy, halogen or trifluoromethyl,
Y is hydrogen, loweralkyl, loweralkoxy, halogen, trifluoromethyl, —S-loweralkyl,

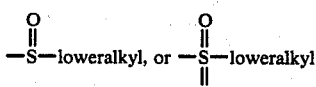

and n is 1 to 3, and
(b) a pharmaceutical acceptable carrier therefor.
12. The composition of claim 11 wherein the compound is [2-amino-3-(2-hydroxyethyl)phenyl]phenylmethanone.
13. The composition of claim 11 wherein the compound is [2-amino-5-chloro-3-(2-hydroxyethyl)phenyl]phenylmethanone.
14. The composition of claim 11 wherein the compound is [2-amino-3-(2-hydroxyethyl)phenyl](4-chlorophenyl)methanone.
15. The composition of claim 11 wherein the compound is [2-amino-3-(2hydroxyethyl)phenyl](4-bromophenyl)methanone.
16. A compound selected from the group having the formula:

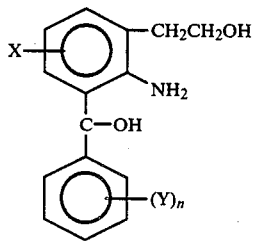

wherein;

X is selected from the group consisting of hydrogen, loweralkyl, loweralkoxy, halogen or trifluoromethyl, Y is selected from the group consisting of hydrogen, loweralkyl, loweralkoxy, halogen and trifluoromethyl, and n is 1–3.

17. A compound of claim 16 which is 2-amino-3-[hydroxy(phenyl)methyl]benzeneethanol.

18. A compound of claim 16 which is 2-amino-5-chloro-3-[hydroxy(phenyl)methyl]benzeneethanol.

19. A compound of claim 16 which is 2-amino-3-[(4-chlorophenyl)hydroxymethyl]benzeneethanol.

20. A compound of claim 16 which is 2-amino-3-[(4-bromophenyl)hydroxymethyl]benzeneethanol.

* * * * *